United States Patent
Highsmith et al.

(10) Patent No.: US 10,231,778 B2
(45) Date of Patent: Mar. 19, 2019

(54) METHODS FOR CONTEMPORANEOUS ASSESSMENT OF RENAL DENERVATION

(71) Applicant: Biosense Webster (Israel) Ltd., Yokneam (IL)

(72) Inventors: Debby Highsmith, Laguna Niguel, CA (US); Kristine Fuimaono, Claremont, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 236 days.

(21) Appl. No.: 14/518,153

(22) Filed: Oct. 20, 2014

(65) Prior Publication Data

US 2016/0106498 A1    Apr. 21, 2016

(51) Int. Cl.
| | |
|---|---|
| *A61B 18/12* | (2006.01) |
| *A61B 18/14* | (2006.01) |
| *A61B 5/04* | (2006.01) |
| *A61N 1/365* | (2006.01) |
| *A61B 18/00* | (2006.01) |

(52) U.S. Cl.
CPC ............ *A61B 18/1492* (2013.01); *A61B 5/04* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/1435* (2013.01); *A61N 1/365* (2013.01)

(58) Field of Classification Search
CPC ...... A61B 18/1492; A61B 2018/00577; A61B 2018/00636; A61B 2018/00642; A61B 2018/00648; A61B 2018/00839; A61B 2018/00404; A61B 2018/00511; A61B 2018/00434; A61B 5/04; A61N 1/365
USPC .................................. 606/41, 42, 34; 607/44
See application file for complete search history.

(56) References Cited

U.S. PATENT DOCUMENTS

| | | | |
|---|---|---|---|
| 5,391,199 A | 2/1995 | Ben-Haim | |
| 5,447,529 A * | 9/1995 | Marchlinski | ....... A61B 18/1492 600/374 |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 9,272,143 B2 * | 3/2016 | Libbus | ............... A61N 1/36114 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2012/0185009 A1 * | 7/2012 | Kornet | ............... A61N 1/36114 607/14 |

(Continued)

FOREIGN PATENT DOCUMENTS

WO    199605768 A1    2/1996

*Primary Examiner* — Thomas A Giuliani
(74) *Attorney, Agent, or Firm* — Dergosits & Noah LLP; Todd A. Noah (57) ABSTRACT

Techniques are disclosed for contemporaneously assessing the success of a renal denervation procedure. One or more characteristics of a patient's heart, such as atrioventricular (AV) interval, PR interval and/or heart rate are monitored during an ablation procedure. A change in the heart characteristic detected during the ablation may indicate successful denervation. Accordingly, successive new locations may be targeted for ablation until a change is detected.

8 Claims, 5 Drawing Sheets

(56) References Cited

U.S. PATENT DOCUMENTS

| | | | |
|---|---|---|---|
| 2013/0303876 A1* | 11/2013 | Gelfand | A61B 18/12 600/407 |
| 2013/0304047 A1 | 11/2013 | Grunewald et al. | |
| 2015/0196762 A1* | 7/2015 | Amurthur | A61N 1/36117 604/21 |

* cited by examiner

METHODS FOR CONTEMPORANEOUS ASSESSMENT OF RENAL DENERVATION

FIELD OF THE PRESENT DISCLOSURE

This disclosure relates to methods for the treatment of hypertension and other medical conditions through targeted ablation of renal nerves accessed through a blood vessel. More particularly, methods for determining whether sufficient denervation has occurred to result in a desired therapeutic effect during the procedure.

BACKGROUND

Radiofrequency (RF) electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical renal ablation procedure involves the insertion of a catheter having an electrode at its distal end into a renal artery in order to complete a circumferential lesion in the artery in order to denervate the artery for the treatment of hypertension. A reference electrode is provided, generally attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the renal artery tissue resulting in formation of a lesion within the renal artery tissue which is electrically non-conductive. The lesion may be formed in the renal artery tissue or in adjacent tissue. During this process, heating of the electrode also occurs as a result of conduction from the heated tissue to the electrode itself Although clinical trials have indicated that renal denervation can result in a statistically significant reduction in blood pressure, challenges are associated with such procedures as conventionally performed. For example, a typical denervation procedure may involve the formation of one or more lesions at desired locations in a patient's renal vasculature intended to sufficiently affect the sympathetic nervous system so that the desired reduction in blood pressure results. However, in order to gauge success, the patient typically needs to be monitored for a significant period of time after the procedure on the order of days or even months to determine whether the desired reduction in blood pressure has been achieved. If the desired result is not obtained, the patient may need to undergo the procedure one or more times until a sufficient reduction is produced. As will be appreciated, this represents an increase in trauma to the patient, cost and recovery time.

Accordingly, it would be desirable to evaluate whether the patient's renal vasculature has been sufficiently denervated while the procedure is being performed. This disclosure satisfies this and other needs, as will be described in the following materials.

SUMMARY

The present disclosure is directed to methods for the treatment of a patient, particularly, for the treatment of hypertension and other associated medical conditions through the ablation of nerves associated with renal activity.

One suitable method for the treatment of a patient includes inserting an ablation catheter into a body of a patient, monitoring a heart characteristic of the patient, ablating tissue at a first targeted location, determining whether the heart characteristic changed during ablation and performing an ablation at a new targeted location if the heart characteristic did not change. Furthermore, ablations may be performed at successive new targeted locations until a change in the heart characteristic is determined during ablation.

In one aspect, monitoring the heart characteristic includes measuring an atrioventricular (AV) interval. For example, determining whether the heart characteristic changed during ablation may include determining whether the AV interval increased.

In one aspect, monitoring the heart characteristic includes measuring a PR interval. For example, determining whether the heart characteristic changed during ablation may include determining whether the PR interval increased.

In one aspect, monitoring the heart characteristic includes measuring the patient's heart rate. For example, determining whether the heart characteristic changed during ablation may include determining whether the patient's heart rate increased.

In another aspect, monitoring the heart characteristic includes at least two of the group consisting of measuring an AV interval, measuring a PR interval and measuring the patient's heart rate.

In yet another aspect, the patient's heart may be paced at a higher frequency than a heart rate in sinus rhythm during ablation.

In some embodiments, the treatment may be for hypertension. The first targeted location may be sympathetic nerves of the patient. Ablating tissue at a first targeted location may at least partially denervate a portion of the patient's renal vasculature. Further, the first targeted location is in a renal artery.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

Figure 1:
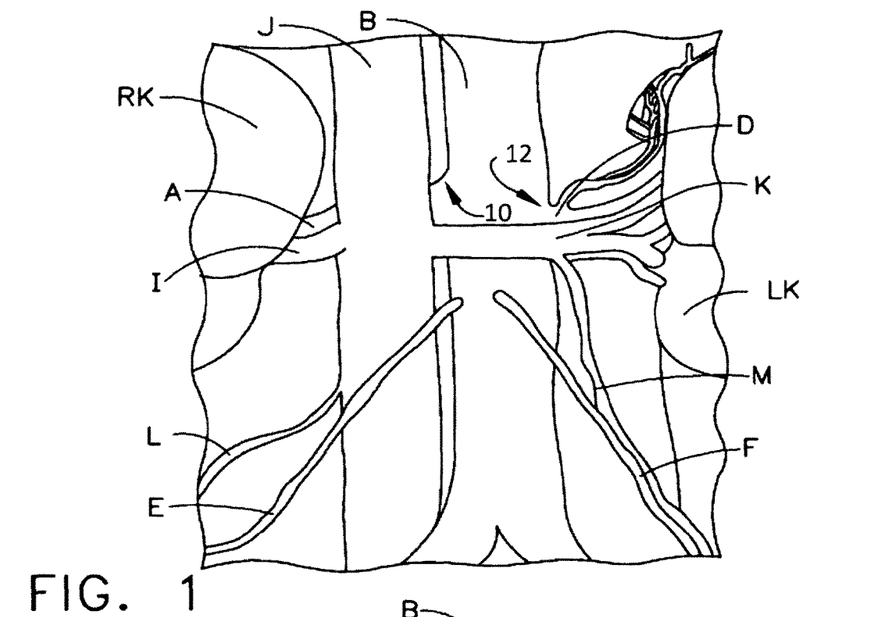
FIG. 1 is a diagram illustrating the abdominal anatomy of a human including the renal veins and arteries and depicting the ablation targets in accordance with the present invention.
Figure 2:
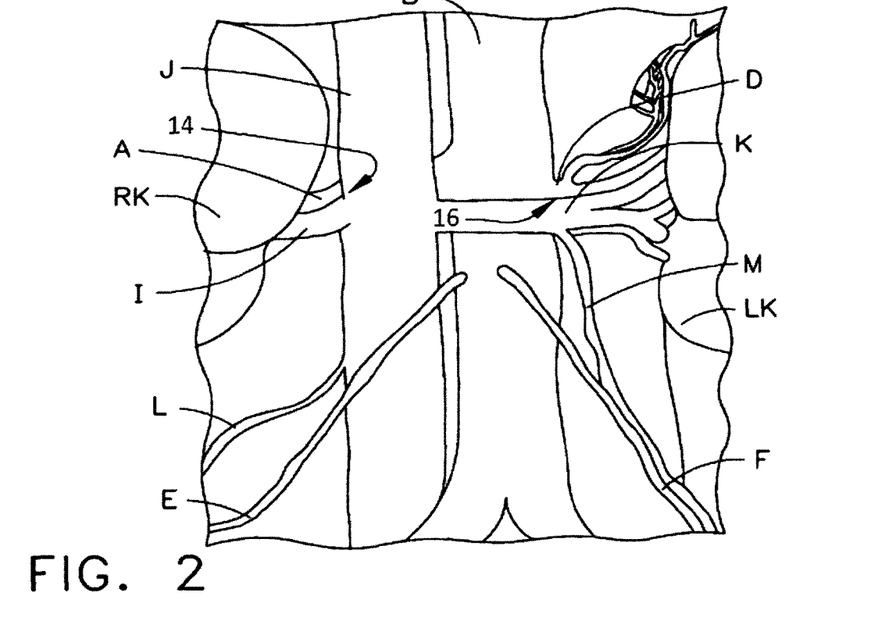
FIG. 2 is a diagram illustrating the abdominal anatomy of a human including the renal veins and arteries and depicting the ablation targets in accordance with the present invention.

Currently renal denervation is performed within a renal vessel and the lesion set may include a helically formed set of lesions within the renal vessel that provides for a complete or nearly complete circumferential lesion around the lumen of the vessel, whether contiguously circumferential or not. FIG. 1 is a diagram showing locations for the targeted ablation of the renal sympathetic nerves in the right and left renal arteries. FIG. 2 is a diagram showing locations for the targeted ablation of the nerves of the right and left renal veins. Further details regarding locations for ablation to cause renal denervation are provided in commonly-assigned U.S. Patent Application Publication 2013/0304047 A1, whose disclosure is incorporated herein by reference.

In FIG. 1, Left and right kidneys (LK and RK) are supplied with oxygenated blood by the right renal artery (A) and left renal arteries (D) which are in turn supplied by the abdominal aorta (B). Despite their relatively small size, the kidneys receive approximately 20% of the total oxygenated blood output of the heart. Each renal artery branches into segmental arteries, dividing further into interlobar arteries which penetrate the renal capsule and extend through the renal columns between the renal pyramids. Urine is excreted by the kidneys LK and RK then to the ureters and then to the bladder of the urinary system. Also shown in FIG. 1 are the right gonadal artery (E) and the left gonadal artery (F).

Once the oxygenated blood is used by the kidneys it flows from the kidneys back to the heart via the right renal vein (I) from the right kidney (RK) and via the left renal vein (K) from the left kidney (LK) through inferior vena cava or "IVC" (J). Also shown in FIG. 2 are the right gonadal vein (L) and the left gonadal vein (M), The kidneys and the central nervous system communicate via the renal plexus, whose fibers course along the renal arteries to reach each kidney. Renal nerves extend longitudinally along the length of and around the renal arteries RA generally within the adventitia of the wall of the artery approximately 3 mm below the endothelial layer.

FIG. 1 depicts exemplary target locations for ablation in the abdominal aorta (H). A catheter is introduced into the abdominal aorta (H) and the ablation targets the nerves from the aorta side. In one embodiment, a length of the artery may be targeted for ablation in a spiral pattern. Other suitable target sites and/or ablation patterns may be employed as desired. FIG. 2 depicts exemplary target locations for ablation near the IVC (B). A catheter is introduced into the IVC and the ablation targets the appropriate nerves from the venous side. Again, a desired target site within the vein may be subjected to an ablation pattern. For example, the right bundle of nerves may be targeted and ablated at a single location in the IVC at the junction of the IVC where the right renal vein branches (I) off from the IVC at 14. To target the left nerves the ablation is performed in the vicinity of a location in the left renal vein where the left renal artery branches from the abdominal aorta at the point where the left renal vein crossed over this branching junction 16. Ablation of the targeted nerves on the right side should occur at the location in the IVC that is nearest spatially to the superior junction between the right renal artery and the abdominal aorta. Likewise, ablation of the targeted nerves on the left side should occur at the location in the left renal vein that is nearest spatially to the superior junction between the left renal artery and the abdominal aorta. The ablation at these locations is meant to ablate through the wall of the IVC or left renal vein to target the nerves that enervate the right and left kidney but reside near the superior junction of the right and left renal arteries as they branch from the abdominal aorta. Although described in the context of ablation relative to the aorta, the renal denervation techniques of this disclosure are applicable to other tissue ablation sites.

Figure 3:
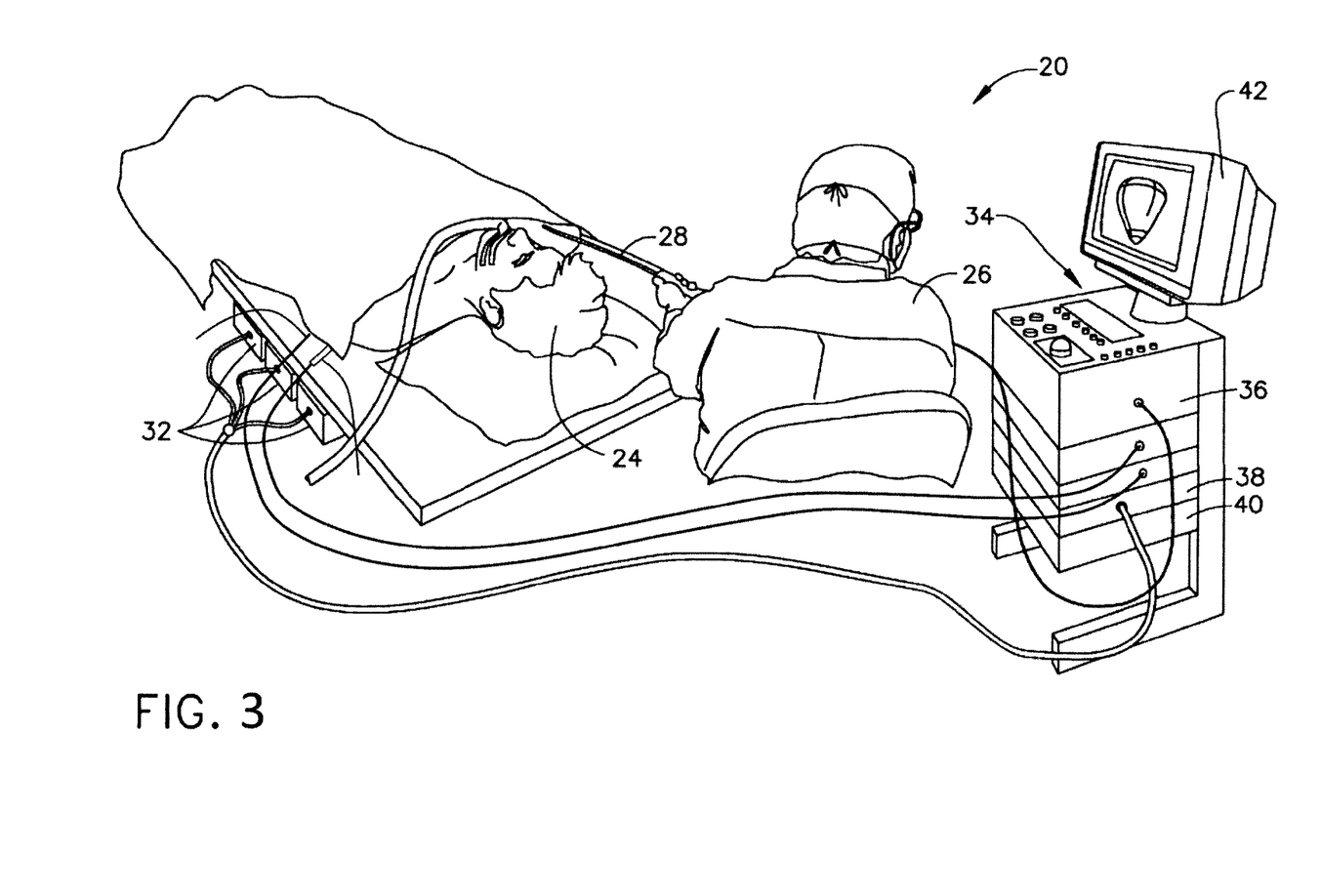
FIG. 3 is a schematic representation of a system for use in practicing a method in accordance with the present invention.

FIG. 3 is a schematic, pictorial illustration of a system 20 for renal and/or cardiac catheterization and ablation, in accordance with an embodiment of the present invention. System 20 may be based, for example, on the CARTO™ mapping systems, produced by Biosense Webster Inc. (Diamond Bar, Calif.) and/or SmartAblate or nMarq RF generators. This system comprises an invasive probe in the form of a catheter 28 and a control and/or ablation console 34. In the embodiment described below, it is assumed that catheter 28 is used in ablating tissue of a patient's vascular wall, as is known in the art.

An operator 26, such as a cardiologist, electrophysiologist or interventional radiologist, inserts ablation catheter 28 into and through the body of a patient 24, such as through a femoral or radial access approach, so that a distal end 30 of the catheter either enters the inferior vena cava or abdominal aorta or contacts the outside of the abdominal aorta. The operator advances the catheter so that the distal section of the catheter engages tissue at a desired location or locations described hereinabove or are otherwise known to be suitable for renal denervation. Catheter 28 is typically connected by a suitable connector at its proximal end to console 34. The console 34 comprises a radio frequency (RF) generator 40, which supplies high-frequency electrical energy via the catheter for ablating tissue in the renal vasculature at the locations engaged by the distal tip, as described further herein. Alternatively, the catheter and system may be configured to perform ablation by other techniques that are known in the art, such as cryo-ablation, ultrasound ablation or ablation through the use of microwave energy or laser light.

Console 34 may also use magnetic position sensing to determine position coordinates of distal end 30 inside the body of the patient 24. For this purpose, a driver circuit 38 in console 34 drives field generators 32 to generate magnetic fields within the body of patient 24. Typically, the field generators comprise coils, which are placed below the patient's torso at known positions external to the patient. These coils generate magnetic fields in a predefined working volume that contains the abdominal aorta near the renal veins and arteries. A magnetic field sensor within distal end 30 of catheter 28 generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end.

Further, operator 26 may insert a multipolar electrode catheter 44 percutaneously through patient 24, such as through the femoral vein using the Seldinger technique, so that a distal end is positioned in the atrium or other desired location in the heart. In one aspect, electrode catheter 44 may be configured to record a His bundle electrogram (HBE). Alternatively, electrode catheter may be configured to record a high right atrial (HRA) electrogram. Other intracardial electrograms may also be used as desired. The electrical signals obtained from the electrodes of catheter 44 may be fed to processor 36 for analysis and output to display 42. Electrodes 46 may be placed at suitable locations on the surface of patient 24, such as the arms and legs, to record an electrocardiogram (ECG). Likewise, electrical signals obtained from electrodes 46 may also may be fed to processor 36 for analysis and output to display 42.

Suitable designs for catheter 28 to perform a renal denervation procedure allow the user to direct the therapy at the desired location with a very stable position. The catheter is used to create a large and deep lesion so that all nerves at that location are denervated. The most advantageous method of energy delivery would be such that the energy delivery would be able to be focused deeper within the adventi tissue and spare as much of the endothelial layer as possible to avoid possible stenosis and also target the nerves in the adventitia as the targeted nerves are not at the surface or in the endothelia. Some known methods of energy delivery that have these characteristics are radiofrequency (RF) ablation catheters (irrigated or non-irrigated), focused ultrasound catheters or laser energy delivery catheters. Optimally the catheter would be able to sit around the renal artery and then ablate just at the juncture point. A balloon, shape memory material structure, or a stabilizing member may be used as the anchoring device within the renal artery or a branch of a vessel to help locate and stabilize the point like ablation device which then is located to side or forward of the anchoring device so that it is stabilized at the desired targeted junction location. Additional details regarding suitable catheter designs for renal denervation are provided in U.S. Patent Application Publication 2013/0304047 A1, which has been incorporated by reference as noted above.

Figure 4:
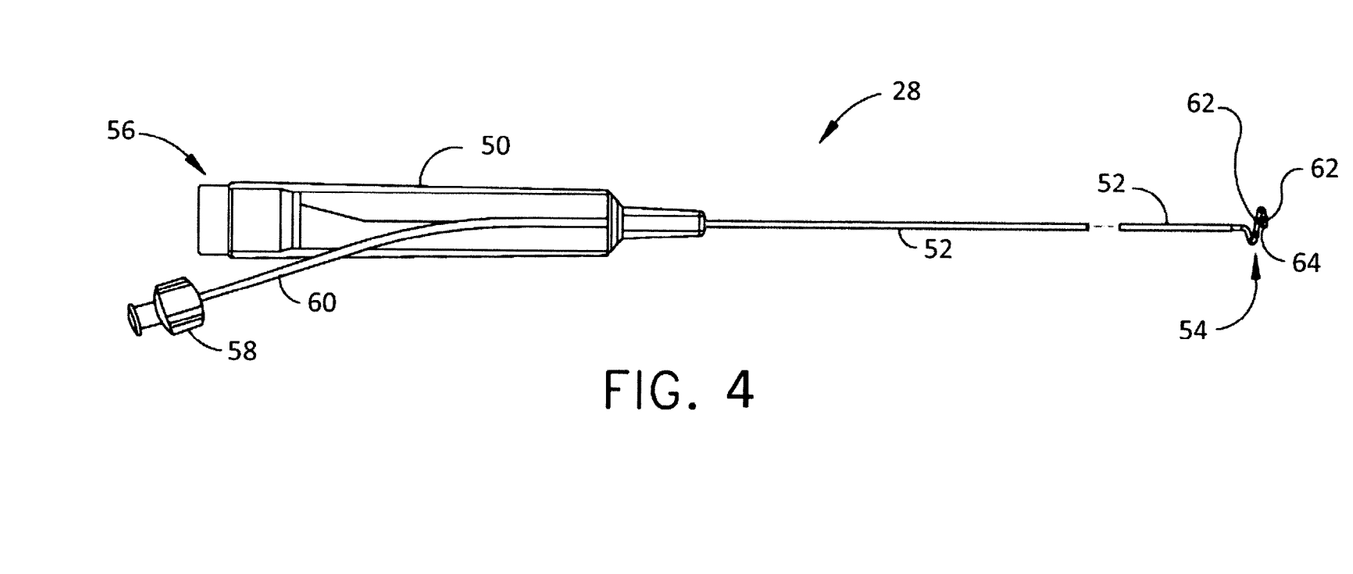
FIG. 4 is a side view of a catheter for use in practicing a method in accordance with the invention.

FIG. 4 depicts an embodiment of a catheter 28 for use in the methods of this disclosure. As shown in side view, catheter 28 may include control handle 50, shaft 52 and distal assembly 54. Control handle 50 may be formed from an injection molded polymer such as polyethylene, polycarbonate or ABS or other similar material and include connector 56 is inserted into the proximal end to provide an electrical connection to a mating connector and cable assembly that is connected to RF generator 40. Irrigation luer hub 58 is a fitting capable of being attached to mating connector from an irrigation source such as an irrigation pump (not shown) to conduct fluid through irrigation side arm 60 to a lumen in shaft 52 to distal assembly 54. Catheter 28 may also be constructed without irrigation. Distal assembly 52 may be a generally helical assembly with a height of approximately 11 millimeters (mm). A plurality of ring electrodes 62, such as six, may be dispersed on the generally circular portion of the distal assembly. The distal most ring electrode 62 being approximately 5 mm from the atraumatic tip 64, which may be a polyurethane plug at the distal tip of distal assembly 54. Each ring electrode is approximately 3 mm in length and is spaced from the next electrode by approximately 4 to 4.5 mm. Each ring electrode 62 is made of a noble metal, preferably a mixture of platinum and iridium although other noble metals such as gold and palladium may also be used, and is connected to a plurality of lead wires. Each ring electrode may be used for visualization, stimulation and ablation purposes. A thermocouple is attached to each ring electrode to provide an indication of the temperature at or near the tissue. RF energy can be delivered either individually to one electrode, simultaneously to more than one electrode or in a bi-polar mode between electrodes. The ring electrodes may be irrigated through a plurality of apertures using fluid supplied through irrigation luer hub 58. The distal assembly may also contain sensors, such as three-axis magnetic location sensors or singles axis (SAS) sensors to facilitate positioning ring electrodes 62 at a desired location in the vasculature of patient 24. Distal assembly 54 may be implemented using a shape memory material such as nitinol which has been pre-formed to assume a desired loop shape when unconstrained at body temperature. The distal tip assembly is sufficiently flexible to permit the loop to straighten during insertion through a sheath (not shown) and then resume the arcuate form when unconstrained. The working length including catheter shaft 52 and distal assembly 54 may be approximately 90 cm for renal ablation, but may vary depending on the application. A fluoro-opaque marker may be placed at or near the distal end of the distal assembly 54 to aid visualization under fluoroscopy.

In use, the catheter assembly 24 is used with a sheath (not shown), such as a steerable sheath or a sheath with an appropriate curve to guide the catheter to the renal vasculature, which facilitates the placement of the catheter in the proper place in the anatomy for the desired ablation/denervation. Once the distal end of catheter 28 exits the sheath, distal assembly 54 may take the pre-configured generally helical shape. The helical shape will provide sufficient apposition of the ring electrodes against the renal vessel wall to provide contact for an ablation that upon the delivery of RF energy from generator 40 to one or more of ring electrodes 62 will result in the denervation or partial denervation of the renal vessel.

As described above, even though ablation may be performed at a target location within the patient's vasculature, there may be insufficient denervation to achieve the intended therapeutic result. Accordingly, the techniques of this disclosure include monitoring a heart characteristic during the ablation procedure to evaluate whether sufficient denervation has occurred. In one aspect, the monitored heart characteristic may be the atrioventricular (AV) interval. In another aspect, the monitored heart characteristic may be the PR interval. In yet another aspect, the monitored heart characteristic may be the patient's heart rate. The above heart characteristics may be used alone or in any combination.

Figure 5:
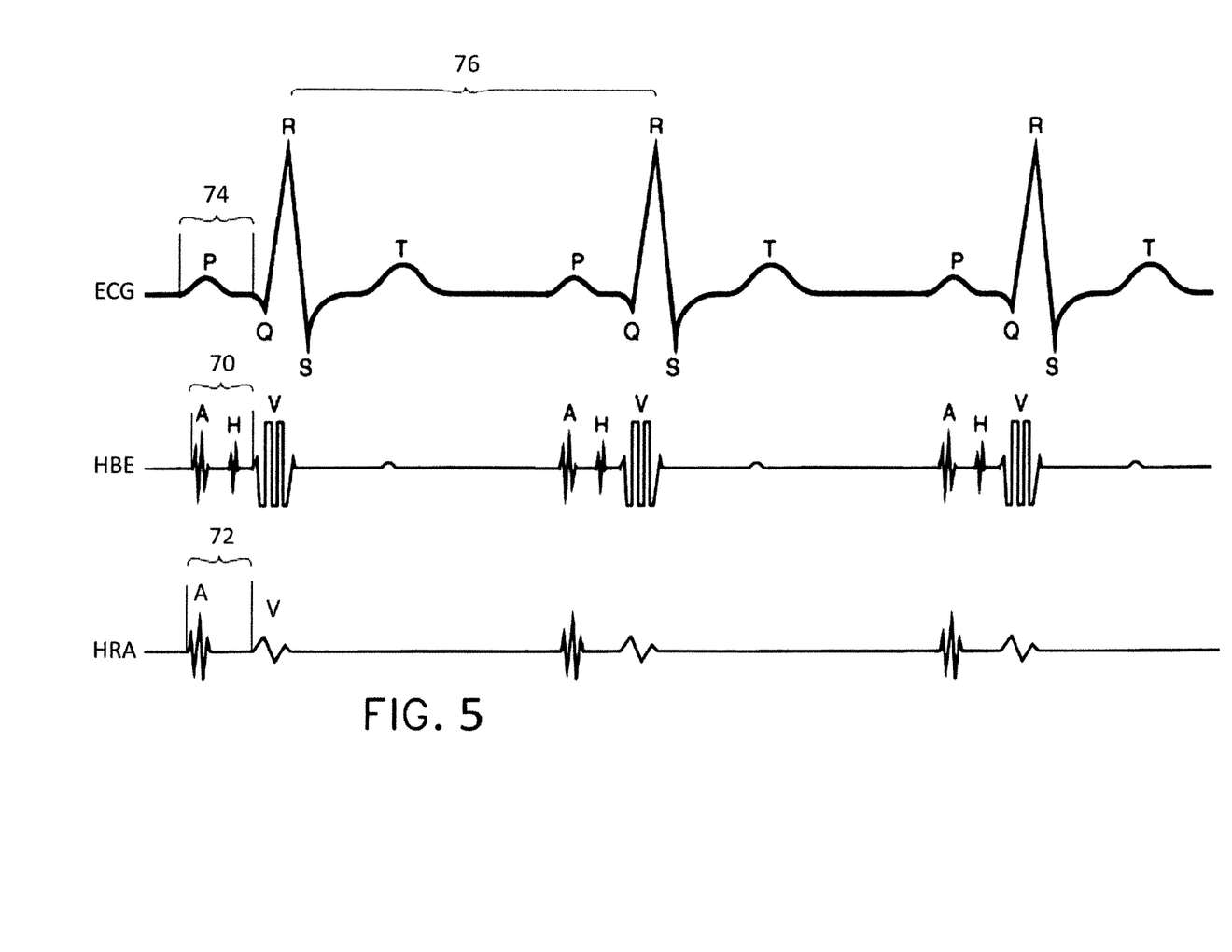
FIG. 5 is a schematic representation of measurements of heart characteristics in accordance with the present invention.

To help illustrate aspects of this disclosure, FIG. 5 shows exemplary ECG and HBE recordings that may be used according to the methods of this disclosure. As shown in the HBE trace, the A wave indicates low right atrial activation, His bundle activity is denoted H and the V deflection indicates ventricular activation. Conventionally, the time period between the onset of A wave and the subsequent onset of the V deflection is known as the AV interval 70. Similarly, in the HRA trace, atrial polarization is denoted A and ventricular polarization is denoted V. AV interval 72 may be measured as the time period between the onset of atrial polarization and the onset of ventricular polarization. Furthermore, as known in the art an ECG trace of a cardiac cycle includes a P wave, a QRS complex and a T wave as shown. Correspondingly, the time period between the onset of the P wave and the onset of the QRS complex is known as the PR interval 72. One of skill in the art will appreciate that heart rate may be determined in any number of suitable ways, including by deriving it from the period between successive portions of the cardiac cycle, such as between the peaks of the QRS complexes 74.

In one aspect, the AV interval may used to assess the acute intraprocedural effects on AV conduction as a parameter indicating a successful denervation. The signals may be monitored pre-ablation, during ablation, and post-ablation and compared. The change in characteristic may be determined as a percentage relative to a baseline established by measurement of the characteristic pre- and/or post-ablation, although other suitable techniques for evaluating change may also be employed. For example, a change in the AV interval during the ablation procedure may indicate successful denervation. In one embodiment, the ablation procedure may be performed and if an increase in the AV interval is monitored during the procedure, the procedure may be concluded or additional treatment may be indicated based on the observed response. The procedure may also be continued until a set number of these increases are observed from a set number of ablation points being approximately 4 but more preferably 5. If an increase is not seen, another electrode may be chosen to administer an ablation or catheter 28 may be repositioned to ablate a different location of the renal vasculature. The process of ablation and relocation may be repeated as desired until a change in the AV interval signals sufficient denervation has occurred. Similarly, the other noted heart characteristics may be monitored during the procedure such that the ablation and relocation process is performed until a sufficient change is monitored during the procedure. For example, a suitable change in the PR interval may be an increase in the PR interval during the procedure. Further, a suitable change in heart rate may be an increase in heart rate.

Table 1 provides experimental heart rate (HR) and PR interval measurements, comparing values obtained before, during and after three ablation procedures, one performed at a left kidney location and two performed at a right kidney location that resulted in successful denervation as indicated by a desired decrease in blood pressure. As can be seen, both heart rate and PR interval increased during the ablation procedure as compared to the before and after measurements.

TABLE 1

| Timing | Left Kidney | | Right Kidney 1 | | Right Kidney 2 | |
| --- | --- | --- | --- | --- | --- | --- |
| Characteristic | HR | PR | HR | PR | HR | PR |
| Pre | 111 | 125 | 111 | 126 | 114 | 128 |
| During @ 15 sec | 114 | 128 | 111 | 126 | 114 | 132 |
| During @ 30 sec | 115 | 131 | 112 | 126 | 114 | 133 |
| During @ 45 sec | 115 | 131 | 111 | 128 | 115 | 133 |
| Post | 111 | 126 | 110 | 128 | 114 | 128 |

In a further aspect, the methods of this disclosure may include pacing at a higher frequency than the heart rate in sinus rhythm to accentuate the change in heart characteristic that is used to evaluate successful denervation. Notably, heart rates have been observed to decrease during renal denervation ablation procedures. Accordingly, pacing may help counteract this effect.

Figure 6:
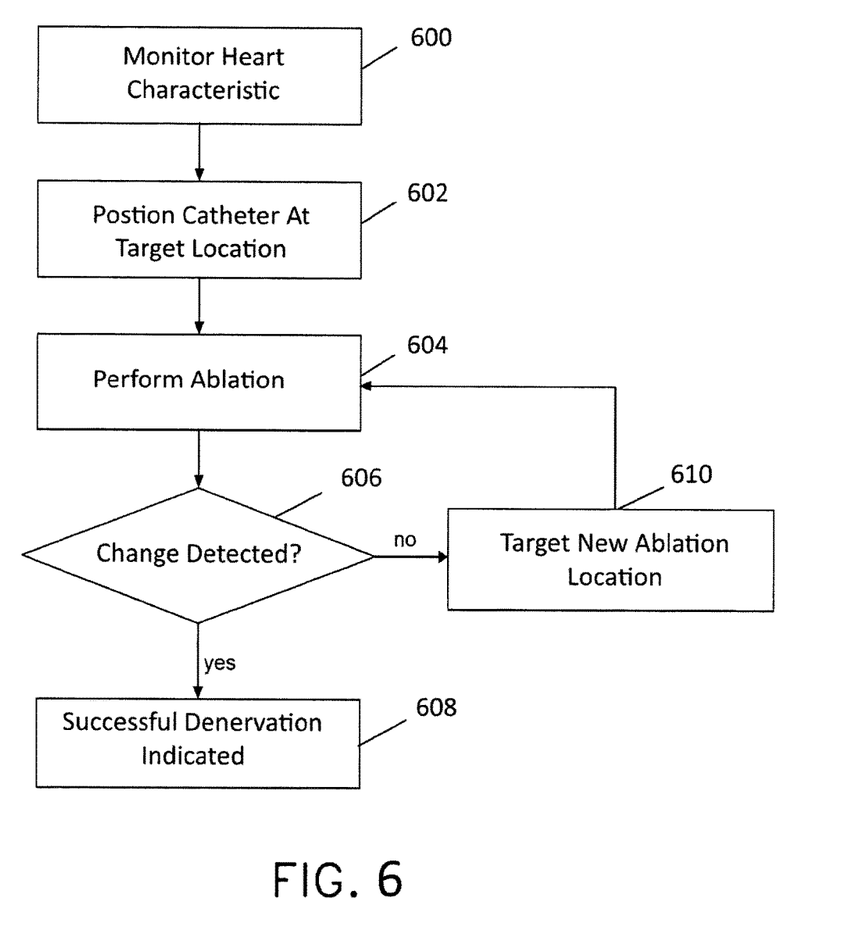
FIG. 6 is a flowchart representing a method in accordance with the present invention.

The flowchart shown in FIG. 6 represents one embodiment of a suitable method according to this disclosure. Starting with 600, monitoring of one or more characteristics of a patient's heart is commenced. In 602, catheter 28 is positioned to form a lesion at a first target location within the renal vasculature. In 604, an ablation is performed to create the lesion. As described above, this may include delivering RF energy through catheter 28 for a designated period of time, such as approximately one minute. If a change in the one or more heart characteristics relative to measurements immediately before and/or after the ablation is detected in 606, it may be determined that successful denervation has occurred as indicated by 608 and the procedure may be concluded. Otherwise, a new ablation target may be selected by repositioning catheter 28 and/or by energizing a different electrode pattern in 610 and the method may return to 604, so that an ablation is performed at the new location and success is reevaluated as described above.

Described herein are certain exemplary embodiments. However, one skilled in the art that pertains to the present embodiments will understand that the principles of this disclosure can be extended easily with appropriate modifications to other applications.

What is claimed is:

1. A method for treatment of a patient comprising: inserting an ablation catheter into a body of the patient; monitoring a heart characteristic of the patient, the heart characteristic comprising a timing characteristic, wherein monitoring the heart characteristic comprises at least two of the group consisting of measuring an AV interval, measuring a PR interval and measuring the patient's heart rate; ablating tissue at a first targeted location; determining, while ablating the tissue, whether the heart characteristic increased during the ablation; and performing an ablation at a new targeted location until the heart characteristic increases when there is no increase in the heart characteristic at the first targeted location.

2. The method of claim 1, further comprising performing ablations at successive new targeted locations until an increase in the heart characteristic at a corresponding one of the new targeted locations is determined during ablation.

3. The method of claim 1, further comprising pacing the patient's heart at a higher frequency during ablation than a heart rate in sinus rhythm.

4. The method of claim 1, wherein the treatment is for hypertension.

5. The method of claim 1, wherein the first targeted location is associated with sympathetic nerves of the patient.

6. The method of claim 5, wherein ablating tissue at a first targeted location at least partially denervates a portion of the patient's renal vasculature.

7. The method of claim 6, wherein the first targeted location is in a renal artery.

8. The method of claim 1, further comprising pacing at a higher frequency to accentuate the monitored heart characteristic.

* * * * *